(12) United States Patent
Matoba et al.

(10) Patent No.: US 7,529,337 B2
(45) Date of Patent: May 5, 2009

(54) ENERGY DISPERSION TYPE RADIATION DETECTING SYSTEM AND METHOD OF MEASURING CONTENT OF OBJECT ELEMENT

(75) Inventors: Yoshiki Matoba, Chiba (JP); Kiyoshi Hasegawa, Chiba (JP); Takayuki Fukai, Chiba (JP)

(73) Assignee: SII Nano Technology Inc., Chiba (JP)

( * ) Notice: Subject to any disclaimer, the term of this patent is extended or adjusted under 35 U.S.C. 154(b) by 47 days.

(21) Appl. No.: 11/820,893

(22) Filed: Jun. 21, 2007

(65) Prior Publication Data

US 2008/0008293 A1  Jan. 10, 2008

(30) Foreign Application Priority Data

Jun. 22, 2006  (JP)  ............................. 2006-172576

(51) Int. Cl.
*G01N 23/223*  (2006.01)
(52) U.S. Cl. .......................................... 378/45; 378/44
(58) Field of Classification Search ................... 378/44, 378/45, 46, 49, 110, 112
See application file for complete search history.

(56) References Cited

U.S. PATENT DOCUMENTS

| | | | | |
|---|---|---|---|---|
| 5,062,127 A | * | 10/1991 | Sayama et al. ................. | 378/45 |
| 6,426,993 B1 | * | 7/2002 | Satoh ........................... | 378/45 |
| 6,512,811 B2 | * | 1/2003 | Fujioka et al. ................. | 378/51 |
| 6,522,718 B2 | * | 2/2003 | Sato .............................. | 378/50 |
| 6,810,106 B2 | * | 10/2004 | Sato .............................. | 378/50 |
| 7,170,970 B2 | * | 1/2007 | Tani et al. ...................... | 378/45 |
| 7,233,645 B2 | * | 6/2007 | Feda ............................. | 378/102 |
| 7,289,598 B2 | * | 10/2007 | Matoba ......................... | 378/46 |
| 7,356,114 B2 | * | 4/2008 | Kataoka et al. ............... | 378/44 |
| 7,428,293 B2 | * | 9/2008 | Fukai et al. ................... | 378/44 |

FOREIGN PATENT DOCUMENTS

JP  5-258693 A  10/1993

* cited by examiner

*Primary Examiner*—Allen C. Ho
(74) *Attorney, Agent, or Firm*—Brinks Hofer Gilson & Lione (57) ABSTRACT

To provide an energy dispersion type radiation detecting system and a method of measuring a content of an object element capable of carrying out a measurement by determining an intensity of an incidence radiation to constitute an optimum minimum limit of detection by restraining an influence of a pile up, the energy dispersion type radiation detecting system includes an incidence system of irradiating the incidence radiation to a sample by a predetermined intensity, a detection system of detecting a radiation emitted from the sample by irradiating the incidence radiation for specifying a content of an object element of the sample based on a spectrum of the detected radiation, and the energy dispersion type radiation detecting system includes a control portion capable of irradiating the incidence radiation by an optimum intensity by determining the optimum intensity of the incidence radiation minimizing a minimum limit of detection of the object element based on the spectrum of the detected radiation.

16 Claims, 3 Drawing Sheets

ENERGY DISPERSION TYPE RADIATION DETECTING SYSTEM AND METHOD OF MEASURING CONTENT OF OBJECT ELEMENT

This application claims priority under 35 U.S.C. §119 to Japanese Patent Application No. JP2006-172576 filed Jun. 22, 2006, the entire content of which is hereby incorporated by reference.

BACKGROUND OF THE INVENTION

1. Field of the Invention

The present invention relates to an energy dispersion type radiation detecting system and a method of measuring a content of an object element for irradiating an incident irradiation of an X-ray, an electron beam or the like to a sample, detecting a radiation of a characteristic X-ray generated from the sample and carrying out an element analysis and a composition analysis of the sample from a spectrum of the radiation.

2. Description of the Related Art

In a related art, as a method of carrying out an element analysis and a composition analysis of a sample, there is a method of irradiating an incidence radiation of an X-ray, or an electron beam from an incidence system to a sample constituting an object, detecting a radiation of a characteristic X-ray or the like generated by exciting an element contained in the sample by the incidence radiation by a detecting system to analyze. Further specifically, for example, when an electron beam is used as the incidence radiation, an electron beam is irradiated to a sample from an electron gun and a characteristic X-ray is detected as a radiation irradiated from the sample. Further, a content of an object element can be specified by detecting an intensity of the characteristic X-ray with regard to a desired object element by a spectrum of the characteristic X-ray. According to a method of specifying the content of the object element from a spectrum analysis of the irradiation irradiated from the sample by using a radiation detecting system having the incidence system and the detecting system, generally, by increasing an intensity of the incidence radiation from the incidence system, also the intensity of the radiation can be increased and a sensitivity can be increased. Therefore, an accurate measurement can be carried out by restraining a minimum limit of detection. Further, when an incidence radiation is constituted by an X-ray, a characteristic X-ray generated by exciting an element contained in a sample by the incidence radiation is referred to as a fluorescent X-ray.

On the other hand, when the intensity of the incidence radiation is increased to be equal to or larger than a predetermined intensity, the radiation is incident on a detection system of a radiation detecting system more than a detectable count number, and therefore, dead time during which the incident radiation cannot be detected is increased. Therefore, generally, an intensity of the incidence radiation is set to an intensity as high as possible within a range in which the dead time becomes 30% through 50%, and there is also proposed an apparatus of automatically setting an intensity of the radiation line such that the dead time falls in the range (refer to, for example, JP-A-5-258693).

Further, in recent years, in a radiation detecting system for detecting a radiation, a function of a detecting system or the like is remarkably promoted, whereas a detectable total counting rate is about 10 kps in a related art, the counting rate is increased up to 10 times through 50 times as much as the counting rate of the related art, and a radiation emitted from the sample can be detected by irradiating an incidence radiation having a higher intensity to a sample.

Figure 4:
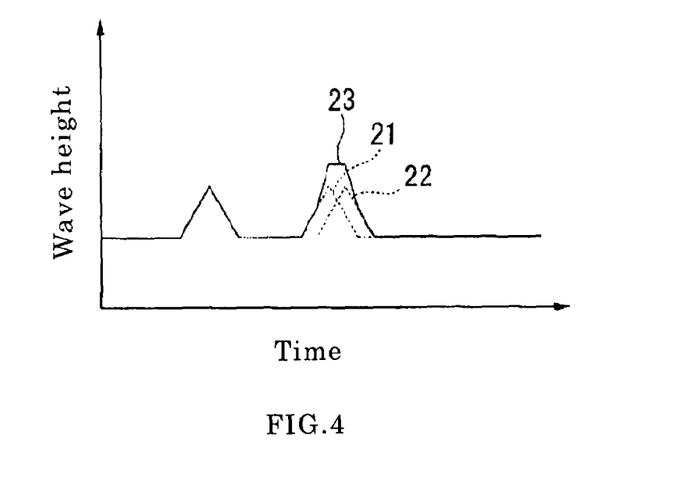
FIG. 4 is an explanatory view showing a principle of generating pile up.

However, even when a radiation having a high intensity is irradiated in the range in which the dead time becomes 30% through 50% in accordance with an increase in the total counting rate of the detecting system, there poses a problem that the detecting system is significantly effected with an influence of pile up. As shown by FIG. 4, pile up is a phenomenon in which when a radiation incident on a detecting system to be counted is detected to process as a pulse signal 21, by overlappingly detecting other pulse signal 22, a height or a width of actually detected pulse signal is deformed as in a pulse signal 23. By generating the pile up, a nonlinear distortion is produced in a spectrum of a detected radiation, and an increase in a background intensity becomes significant. Therefore, there poses a problem that even when the incidence radiation is constituted by the high intensity within the range in which the dead time becomes 30% through 50%, as a result, a minimum limit of detection is increased and an accurate measurement cannot be carried out.

SUMMARY OF THE INVENTION

The invention has been carried out in view of the above-described situation and provides an energy dispersion type radiation detecting system and a method of measuring a content of an object element capable of carrying out a measurement by determining an intensity of an incidence radiation to constitute an optimum minimum limit of detection by restraining an influence of a pile up.

In order to resolve the above-described problem, the invention proposes the following means.

The invention provides an energy dispersion radiation detecting system comprising an incidence system for irradiating an incidence radiation to a sample by a predetermined intensity, and a detecting system for detecting a radiation emitted from the sample by irradiating the incidence radiation for specifying a content of an object element of the sample based on a spectrum of the detected radiation, the energy dispersion type radiation detecting system comprising a control portion capable of irradiating the incidence radiation by an optimum intensity by determining the optimum intensity of the incidence radiation minimizing a minimum limit of detection of the object element based on the spectrum of the detected radiation.

The invention provides a method of measuring a content of an object element for specifying a content of an object element of a sample based on a spectrum of a detected radiation by detecting a radiation emitted from the sample by irradiating an incidence radiation to the sample by a predetermined intensity, the method comprising an initial detecting step of detecting an initial radiation emitted from the sample by irradiating the incidence radiation to the sample by a predetermined initial intensity, an incidence radiation intensity determining step of determining an optimum intensity of the incidence radiation minimizing a minimum limit of detection of the object element based on the spectrum of the detected initial radiation, and a regular detecting step of specifying the content of the object element from the spectrum of the radiation by detecting the radiation emitted from the sample by irradiating the incidence radiation by the optimum intensity.

According to the energy dispersion type radiation detecting system and the method of measuring a content of an object element according to the invention, first, the incidence radiation from the incidence system is irradiated to the sample by the predetermined initial intensity as the initial detecting step. Further, the initial radiation emitted by exciting the sample is detected by the detecting system. Next, the optimum intensity of the incidence radiation minimizing the minimum limit of detection of the object element can be determined based on the spectrum of the detected initial radiation of the control portion as the incidence radiation intensity determining step. Therefore, when the incidence radiation is irradiated to the sample by the optimum intensity as the regular detecting step, the content of the object element can accurately be measured under the optimum minimum limit of detection by irradiating the incidence radiation having the high intensity to the sample while restraining an increase in the background intensity caused by the pile up.

Further, in the energy dispersion type detecting system, it is further preferable that the control portion comprises analyzing means for calculating a sensitivity of the object element, a first background intensity caused by a pile up and a second background intensity caused by other than the pile up in an energy of the radiation in correspondence with the object element and a rate of dead time of the detecting system when the radiation is detected from the spectrum of the detected radiation, and incidence radiation intensity determining means for calculating the optimum intensity of the incidence radiation minimizing the minimum limit of detection of the object element based on the sensitivity, the first background intensity, the second background intensity, and the rate of the dead time.

Further, in the method of measuring a content of an object element, it is further preferable that the incidence radiation intensity determining step comprises a first step of calculating a sensitivity of the object element, a first background intensity caused by a pile up and a second background intensity caused by other than the pile up in an energy of the initial radiation in correspondence with the object element, and a rate of dead time in the initial detecting step from the spectrum of the detected initial radiation, and a second step of calculating the optimum intensity of the incidence radiation minimizing a minimum limit of detection of the object element based on the calculated sensitivity, the calculated first background intensity, the calculated second background intensity, and the calculated rate of the dead time.

According to the energy dispersion type radiation detecting system and the method of measuring a content of an object element, in the incidence radiation intensity determining step, first, at the first step, the control portion calculates the sensitivity of the object element from the spectrum of the detected initial radiation by the analyzing means. Further, the background intensity in the energy in correspondence with the object element in the spectrum of the initial radiation is calculated by being divided into the first background intensity caused by the pile up and the second background intensity caused by other than the pile up. Further, as the second step, by calculating the optimum intensity of the incidence radiation minimizing the minimum limit of detection of the object element based on the calculated result, the minimum limit of detection of the object element is made to be optimum by restraining the influence by the pile up and the content of the object element can accurately be measured.

Further, in the energy dispersion type detecting system, it is further preferable that the incidence radiation intensity determining means of the control portion sets the optimum intensity by multiplying an intensity of the incidence radiation irradiated when the spectrum of the radiation is detected by $\alpha$, substituting a value constituted by multiplying the calculated sensitivity by $\alpha$ for a calculation equation of the minimum limit of detection DL as shown in <Equation 1> as the sensitivity S, substitutes a value constituted by multiplying the calculated rate of the dead time by $\alpha$ therefor as the dead time $\tau$, and substituting a sum of a value constituted by multiplying the first background intensity by $\alpha^2$ and a value constituted by multiplying the second background intensity by $\alpha$ therefor as a background intensity Ib, calculates the coefficient $\alpha$ showing a minimum value of the minimum limit of detection DL, and determines the optimum intensity.

Further, in the method of measuring a content of an object element, it is further preferable that the second step of the incidence radiation intensity determining step sets the optimum intensity by multiplying an initial intensity of the incidence radiation irradiated when the spectrum of the initial radiation is detected by $\alpha$, substitutes a value of multiplying the calculated sensitivity by $\alpha$ for an equation of the minimum limit of detection DL shown in <Equation 1> as a sensitivity S, substitutes a value of multiplying the calculated rate of the dead time by $\alpha$ therefor as the dead time $\tau$, further substitutes a sum of a value of multiplying the first background intensity by $\alpha^2$ and a value of multiplying the second background intensity by $\alpha$ therefor as a background intensity Ib, calculates the coefficient $\alpha$ showing a minimum value of the minimum limit of detection DL, and determines the optimum intensity.

$$DL = \frac{3 \cdot \sqrt{Ib/T \cdot (1-\tau)}}{S} \qquad \text{Equation 1}$$

where a notation Ib designates a background intensity, a notation T designates a measurement time period, a notation S designates a sensitivity, and a notation $\tau$ designates a rate of the dead time.

According to the energy dispersion type radiation detecting system and the method of measuring a content of an object element according to the invention, in the calculation equation shown in <Equation 1>, the coefficient $\alpha$ by which the minimum limit of detection DL indicates a minimum value is determined, and the optimum intensity can be constituted by the initial intensity multiplied by $\alpha$. Here, in the radiation emitted from the sample, the sensitivity of the object element is proportional to the intensity of the incidence radiation. Further, also the rate of the dead time is similarly proportional to the intensity of the incidence radiation. Further, also the second background intensity caused by other than the pile up is similarly proportional to the intensity of the incidence radiation. On the other hand, the first background intensity caused by the pile up is proportional to the square of the intensity of the incidence radiation. That is, by substituting the value of the sensitivity detected in the initial detecting step for the calculation equation shown in <Equation 1> as the sensitivity S, substituting the value of the rate of the dead time in the initial detecting step multiplied by $\alpha$ therefor as the rate $\tau$ of the dead time, substituting the sum of the value of the first background intensity multiplied by $\alpha^2$ and the value of the second background intensity multiplied by $\alpha$ therefor as the background intensity Ib, and determining the coefficient $\alpha$ constituting a minimum value of the minimum limit of detection DL, the content of the object element can accurately be measured by making the minimum limit of detection of the object element optimum by restraining the influence of the pile up.

Further, in the energy dispersion type detecting system, it is further preferable that a plurality of the object elements contents of which are to be specified can be set, the analyzing means of the control portion calculates net intensities of the respective object elements from the spectrum of the detected radiation to be able to search the object element minimizing the net intensity, and the incidence radiation intensity determining means calculates the optimum intensity of the incidence radiation based on the sensitivity of the object element, the first background intensity, and the second background intensity minimizing the net intensity.

Further, in the method of measuring a content of an object element, it is further preferable that there are a plurality of the object elements contents of which are to be specified, at the first step of the incidence radiation intensity determining step, net intensities of the respective object elements are calculated from the spectrum of the detected initial radiation, the sensitivity, the first background intensity, and the second background intensity are calculated for the object element minimizing the net intensity, and at the second step, the optimum intensity of the incidence radiation is calculated based on the sensitivity, the first background intensity, and the second background intensity of the object element minimizing the net intensities.

According to the energy dispersion type radiation detecting system and the method of measuring a content of an object element according to the invention, in the first step of the incidence radiation intensity determining step, by calculating the net intensities of the respective object elements by the analyzing means of the control portion, the object element minimizing the net intensity, that is, minimizing the content can be selected. Therefore, at the second step, by the incidence intensity determining means, the optimum intensity of the incidence radiation is calculated based on the sensitivity of the object element, the first background intensity and the second background intensity, and therefore, the measurement can accurately be carried out for all of the object elements.

Further, in the energy dispersion type detecting system, it is further preferable that the incidence system is constituted by an X-ray tube capable of irradiating a primary X-ray as the incidence radiation, and the control portion is capable of controlling a current supplied to the X-ray tube and sets the primary X-ray irradiated from the X-ray tube to the optimum intensity by adjusting the current.

According to the energy dispersion type radiation detecting system according to the invention, based on the optimum intensity determined by the incidence radiation intensity determining means, the primary X-ray can be irradiated by the optimum intensity as the incidence radiation by controlling the current supplied to the X-ray tube constituting the incidence system.

According to the energy dispersion type radiation detecting system of the invention, the optimum intensity of the incidence radiation can be determined based on the spectrum of the detected radiation by the control portion, and therefore, the content of the object element can be specified by the optimum minimum limit of detection by restraining the influence of the pile up by irradiating the incidence radiation by the optimum intensity.

Further, according to the method of measuring a content of an object element of the invention, the optimum intensity can be determined in the incidence radiation intensity determining step based on the spectrum of the initial radiation in the initial detecting step, and therefore, the content of the object element can be specified by the optimum minimum limit of detection by restraining the influence of the pile up by irradiating the incidence radiation by the optimum intensity.

DETAILED DESCRIPTION OF THE PREFERRED EMBODIMENTS

Figure 1:
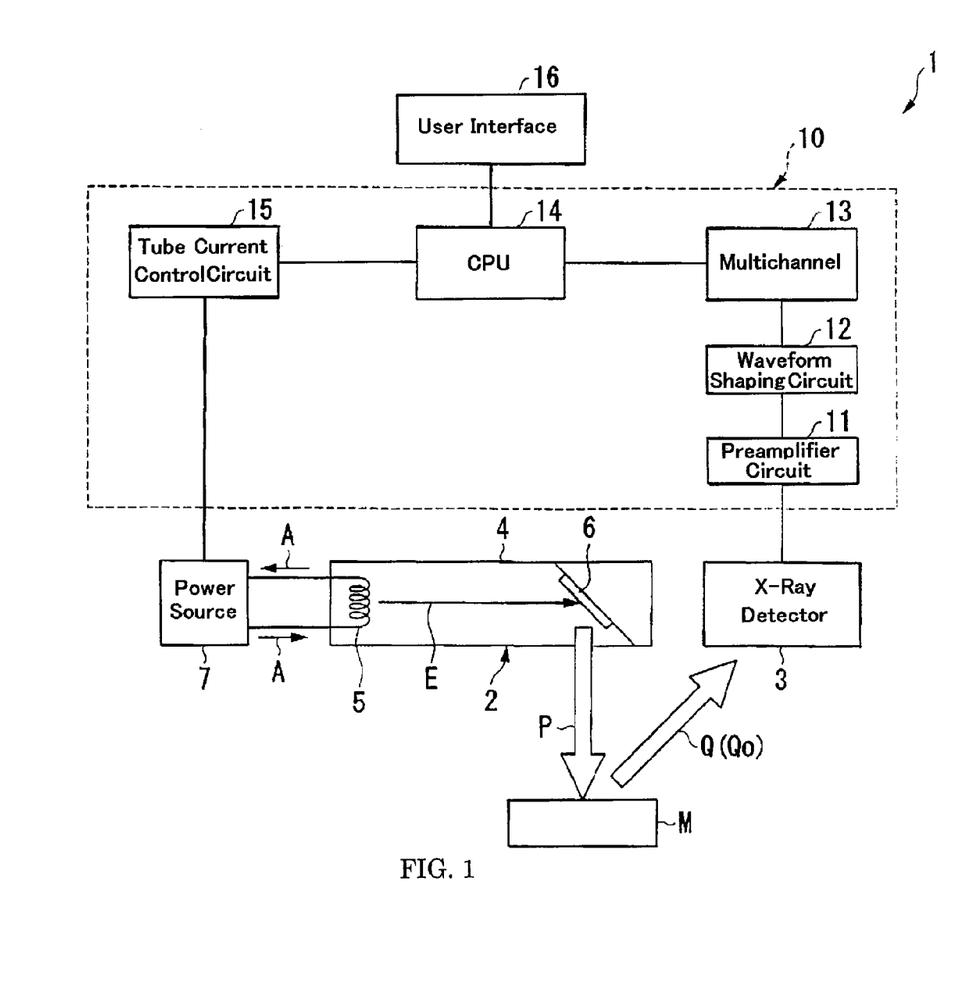
FIG. 1 is a block diagram showing an outline of an energy dispersion type radiation detecting system of an embodiment of the invention.
Figure 2:
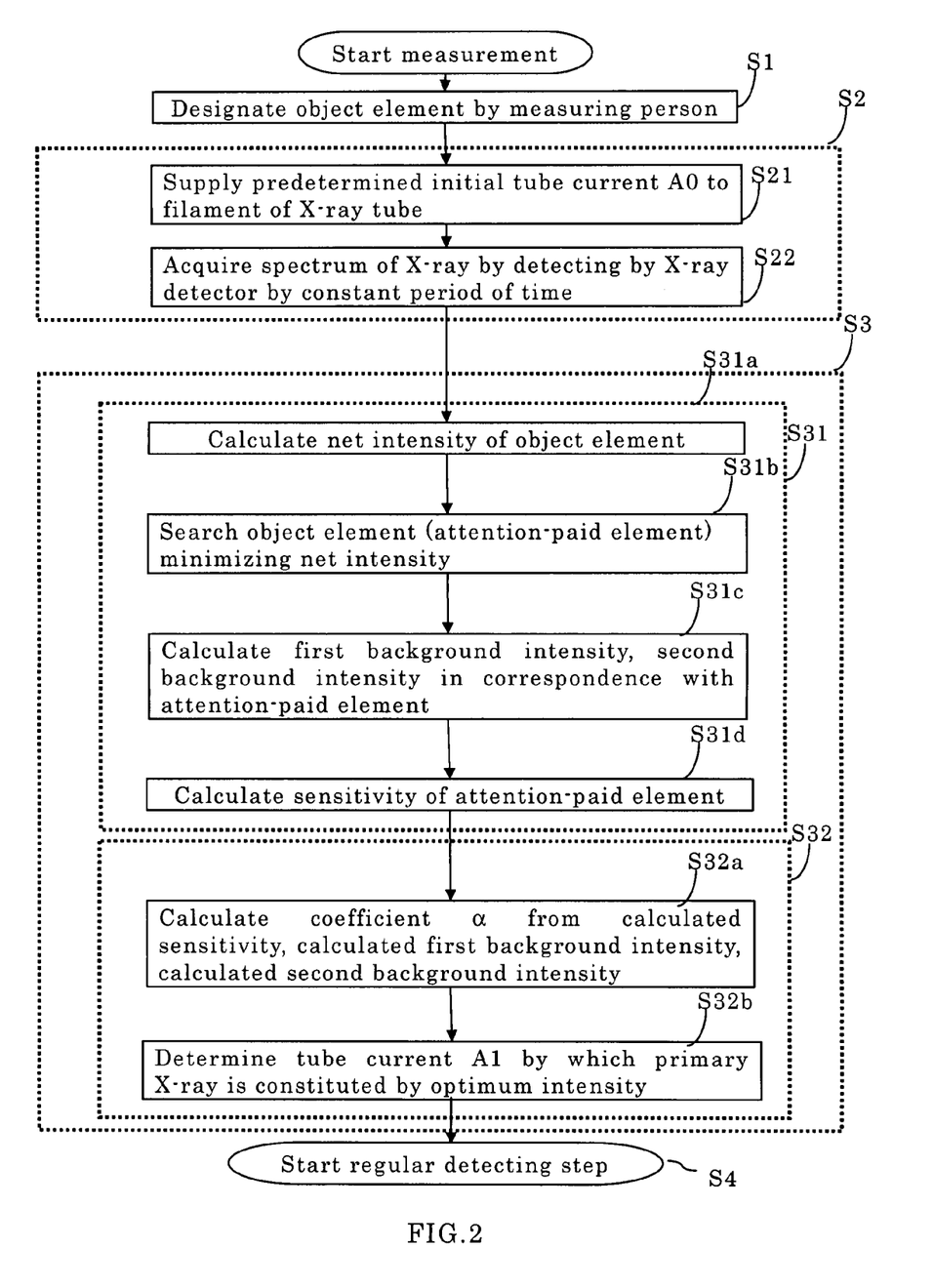
FIG. 2 is a flowchart showing a measuring method in the energy dispersion type radiation detecting system of the embodiment of the invention.
Figure 3:
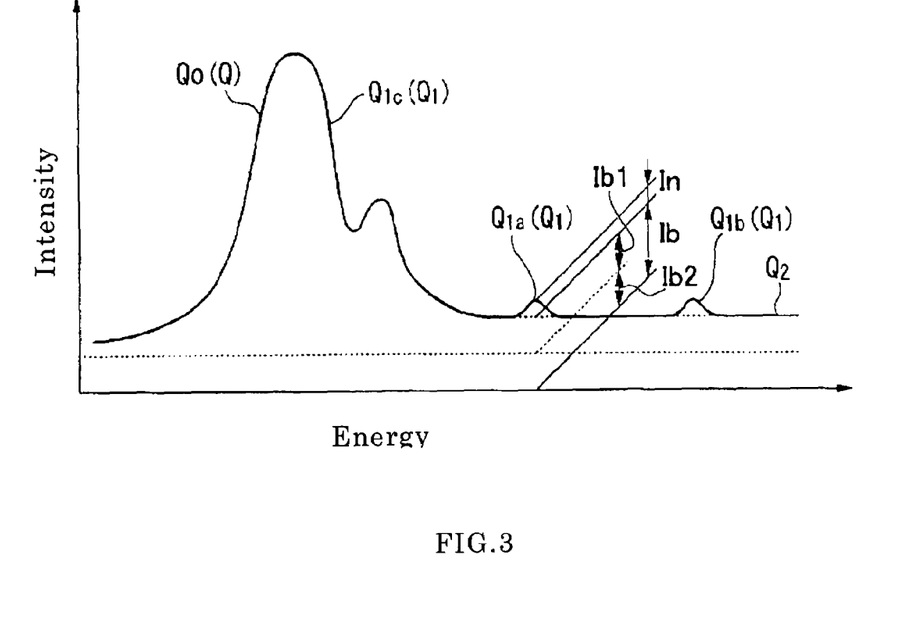
FIG. 3 is a graph showing an example of a spectrum of a fluorescent X-ray detected by the energy dispersion type radiation detecting system of the embodiment of the invention.

FIG. 1 through FIG. 3 show an embodiment according to the invention. As shown by FIG. 1, an energy dispersion type radiation detecting system 1 of the embodiment is a fluorescent X-ray analysis apparatus of an energy dispersion type including an X-ray tube 2 for irradiating a primary X-ray P constituting an incidence radiation to a sample M as an incidence system, and an X-ray detector 3 for detecting a fluorescent X-ray Q (characteristic X-ray) which is a radiation and generated and emitted from the sample M as a detecting system. The X-ray tube 2 includes a vacuum tube 4, a filament 5 provided on one side and a target 6 provided on other end side to be opposed to the filament 5 at inside of the vacuum tube 4. The filament 5 is connected to a power source 7 by which a predetermined tube current A can be supplied. Further, as the target 6, tungsten, rhodium, molybdenum, chromium or the like can be selected. Further, inside of the vacuum tube 4 is provided with an anode on the one end side at which the filament 5 is provided and a cathode on the other end side in which the target 6 is provided and a voltage can be applied there between, although not illustrated.

That is, by supplying the tube current A from the power source 7 to the filament 5 and applying the voltage between both electrodes, an electron beam E emitted from the filament 5 is irradiated to the target 6. Thereby, the target 6 is excited and the primary X-ray P can be irradiated to the sample M disposed to be opposed to the target 6. Further, a collimator or a filter is provided between the X-ray tube 2 and the sample M and the primary X-ray P can be irradiated by a predetermined irradiation range and by a predetermined energy, although not illustrated. Here, an incidence intensity Ip (intensity) of the primary X-ray P is proportional to an intensity of the electron beam E. Further, the intensity of the electron beam E is controlled by the tube current A supplied to the filament 5. That is, by controlling the tube current A supplied by the power source 7, the incidence intensity Ip of the primary X-ray P irradiated to the sample M can be controlled.

The X-ray detector 3 is a semiconductor detector, formed by, for example, an Si element and can output the detected fluorescent X-ray Q as a current pulse having a magnitude in proportion to an energy thereof. Further, the power source 7 of the X-ray tube 2 and the X-ray detector 3 are connected to a control portion 10, the X-ray tube 2 can irradiate the primary X-ray P by the predetermined incidence intensity Ip under control by the control portion 10, further, by the control portion 10, the fluorescent X-ray Q detected by the X-ray detector 3 is analyzed, and based on a result of the analysis, a content of an object element contained in the sample M can be specified. Details of the control portion 10 will be explained as follows.

The control portion 10 includes a preamplifier circuit 11, a waveform shaping circuit 12, and a multichannel 13 connected successively from the X-ray detector 3, and a signal processed thereby is inputted to CPU 14. The current pulse outputted based on the fluorescent X-ray Q detected by the X-ray detector 3 is amplified by the preamplifier circuit 11 and is converted into a voltage pulse. The converted voltage pulse is inputted to the waveform shaping circuit 12, amplified further by the waveform shaping circuit 12, subjected to a processing of shaping a form of the pulse to a triangular or trapezoidal waveform and is inputted to the multi-channel 13. At the multichannel 13, the voltage pulse successively inputted in accordance with detection of the fluorescent X-ray Q is classified for respective magnitudes of pulses in correspondence with an energy of the fluorescent X-ray Q and a number of pulses in correspondence with the intensity of the fluorescent X-ray Q can be recorded. That is, by carrying out the processing continuously for a constant period of time, CPU 14 connected to the multichannel 13 can acquire a spectrum (relationship between energy and intensity) of the fluorescent X-ray Q in the sample M. Further, a tube current control circuit 15 is connected between CPU 14 and the power source 7 of the X-ray tube 2, and the tube current A supplied from the power source 7 to the filament 5, that is, the incidence intensity Ip of the primary X-ray P can be controlled under control by CPU 14. Further, the control portion 10 is provided with a timer and a measurement time period can be recorded thereby, although not illustrated. Further, CPU 14 is connected with a user interface 16 and is connected with a monitor or an operating portion, not illustrated. Therefore, in the monitor, the spectrum of the detected fluorescent X-ray Q and a result of the analysis can be monitored, further, in the operating portion, various operations, for example, input of an object element to be specified can be carried out by way of CPU 14.

CPU 14 includes analyzing means capable of calculating a net intensity In and a sensitivity S of an object element as well as a background intensity Ib in the energy of the fluorescent X-ray of the object element based on the spectrum of the acquired fluorescent X-ray Q and calculating a rate $\tau$ of dead time in the X-ray detector 3 when the fluorescent X-ray Q is detected. Further, CPU 14 includes incidence radiation intensity determining means capable of calculating a minimum limit of detection DL of an object element by a calculation equation of <Equation 2> based on the sensitivity X, the background intensity Ib and the rate $\tau$ of the dead time calculated by the analyzing means and a measurement time period T made to be necessary for actual measurement and capable of determining the incidence intensity of the primary X-ray P minimizing the minimum limit of detection DL by the object element by restraining the influence of the pile up, that is, an optimum incidence intensity If (optimum intensity). An explanation will be given of details of a method of measuring the content of the object element of the sample M by determining the optimum incidence intensity by the analyzing means and the incidence radiation intensity determining means of CPU 14.

$$DL = \frac{3 \cdot \sqrt{Ib/T \cdot (1-\tau)}}{S} \qquad \text{Equation 2}$$

FIG. 2 shows a measurement flow for measuring the content of the object element by determining the optimum incidence intensity If in correspondence with the object element according to the embodiment. As shown by FIG. 2, first, an operator designates a desired object element to CPU 14 from the operating portion, not illustrated, by way of the user interface 16 as an object element determining step S1. Although there may be a single or a plurality of object element(s), according to the embodiment, an explanation will be given of a case of designating, for example, copper (Cu) and lead (Pb) and strontium (Sr). First, as initial detecting step S2, CPU 14 irradiates the primary X-ray P from the X-ray tube 2 to the sample M as initial intensity I0 by constituting the tube current A supplied from the power source 7 to the filament 5 as a previously arbitrary set initial tube current A0 (step S21). At this occasion, an initial fluorescent X-ray Q0 (initial radiation) emitted from the sample M is detected by the X-ray detector 3. Further, CPU 14 acquires a spectrum of an initial fluorescent X-ray Q0 respectively processed by the preamplifier 11, the waveform shaping circuit 12, and the multichannel 13 (step S22). FIG. 3 shows the spectrum of the initial fluorescent X-ray Q0.

As shown by FIG. 3, the spectrum of the acquired fluorescent X-ray Q is classified into a fluorescent X-ray Q1 (Q1a, Q1b, Q1c or the like) caused by a specific element and a scattering X-ray Q2 detected continuously in a range of a total energy. An energy of the fluorescent X-ray is inherent to an element, and a kind of an element contained in the sample M can be specified by a range of an energy of detecting the fluorescent X-ray. In FIG. 3, notation Q1a designates L$\alpha$ radiation of lead (Pb), notation Q1b designates K$\alpha$ radiation of strontium (Sr), notation Q1c designates K$\alpha$ radiation of copper (Cu). Further, the net intensity In constituting the intensity of the fluorescent X-ray Q1 depends on a content of a contained element, that is, the content of the element can be specified by the net intensity In. On the other hand, the background intensity Ib constituting the intensity of the scattering X-ray is an intensity by the scattering X-ray detected by being caused by other than the element contained in the sample M or noise of the detector, and is constituted by a background intensity Ib1 generated by being caused by pile up and a second background intensity Ib2 generated by being caused by other than pile up such as scattering X-ray or the like.

Here, the more increased the incidence intensity Ip of the primary X-ray P irradiated to the sample M, the more increased all of the net intensity In, the first background intensity Ib1, and the second background intensity Ib2. Whereas the net intensity In and the second background intensity Ib2 are increased in proportion to the incidence intensity Ip of the primary X-ray, the first background intensity Ib1 caused by pile up is proportional to a square of the incidence intensity Ip of the primary X-ray. That is, the background intensity Ib is rapidly increased by being caused by pile up in accordance with an increase in the incidence intensity Ip of the primary X-ray. Further, the sensitivity S in a certain object element is calculated by a calculation equation shown by <Equation 5> by the net intensity In. Here, notation C designates a concentration (content) of the object element in the sample M. Therefore, the sensitivity S is inversely proportional to a content of the object element and shows a large value in proportion to the incidence intensity Ip of the primary X-ray P. On the other hand, as shown by <Equation 4> mentioned above, the minimum limit of detection DL is inversely proportional to the sensitivity S and is proportional to a root of the background intensity Ib. That is, whereas the minimum limit of detection DL shows a small value by increasing the value of the intensity S until the incidence intensity Ip of the primary X-ray P is increased to a constant magnitude, when the incidence intensity Ip of the primary X-ray P is increased by a constant or more, an increase in the background intensity Ib becomes significant and the minimum limit of detection DL is increased by the influence of the first background Ib1 caused by pile up.

$$S = \frac{In}{C} \qquad \text{Equation 3}$$

where S sensitivity, In: net intensity, c: concentration.

That is, although the content can be specified by calculating the net intensity In of the object element from the spectrum of the fluorescent X-ray Q detected by initial detecting step S2, the net intensity In calculated at a current stage is not of a case of constituting the minimum limit of detection DL by an optimum value in consideration of the influence of pile up. Therefore, the content of the object element is specified by determining the optimum incidence intensity If of the primary X-ray P minimizing the minimum limit of detection DL in consideration of the influence of pile up based on incidence radiation intensity determining step S3 shown below.

First, as first step S31, analyzing means of CPU 14, reads a net intensity In of each object element from a spectrum of the initial fluorescent X-ray Q0 (S31*a*). Next, by comparing the net intensities In of the respective object elements, the object element minimizing the net intensity In is searched (step S31*b*). Here, assume that, for example, the net intensity In of lead (Pb) is minimum in the object elements. Further, by constituting an attention-paid element by lead (Pb) minimizing the net intensity In, the optimum incidence intensity If is determined by constituting a reference thereby. Next, the analyzing means of CPU 14 calculates the first background intensity Ib1 and the second background intensity Ib2, the rate τ of dead time, as well as the sensitivity S of the attention-paid element in an energy of the fluorescent X-ray Q0 of the attention-paid element. First, a value of the background intensity Ib is read from the acquired spectrum of the initial fluorescent X-ray Q0 (step S31*c*). As described above, the background intensity Ib is a sum of the first background intensity Ib1 and the second background intensity Ib2 and is shown by a calculation equation of <Equation 6>.

$$Ib = Ib1 + Ib2 \qquad \text{Equation 4}$$

Next, CPU 14 changes the incidence intensity Ip of the primary X-ray P by an arbitrarily determined rate β, thereby, similarly acquires a spectrum of the fluorescent X-ray Q and reads a background intensity Ib' in correspondence with the attention-paid element. Here, as described above, the first background intensity Ib1 is proportional to the incidence intensity Ip of the primary X-ray P, the second background intensity Ib2 is proportional to a square of the incidence intensity Ip, and therefore, a relationship between the background intensity Ib' when the incidence intensity Ip of the primary X-ray P is changed by the rate β and the first background intensity Ib1 and the second background intensity Ib2 before being changed is shown by a calculation equation of <Equation 5> by the rate β

$$Ib' = \beta^2 \cdot Ib1 + \beta \cdot Ib2 \qquad \text{Equation 5}$$

Therefore, when the calculated respective background intensities Ib, Ib' and the rate β are made to substitute for respective calculation equations of <Equation 4> and <Equation 5>, the first background intensity Ib1 and the second background intensity Ib2 in the energy of attention-paid element detected by irradiating the primary X-ray P by the initial intensity I0 can be calculated.

Next, by the analyzing means of CPU 14, the sensitivity S of the attention-paid element is calculated (step S31*d*). The sensitivity S is calculated by a fundamental parameter method from the acquired spectrum of the initial fluorescent X-ray Q0. The fundamental parameter method is a publicly-known operating method for predicting the sensitivity S of a certain element in a sample a composition of which is unknown, and is a method of predicting the concentration C and the sensitivity S of the object element by repeatedly comparing the net intensity In of the attention-paid element read from the spectrum of the initial fluorescent X-ray Q0 and a net intensity in a calculation calculated based on the predicted concentration C.

Next, as second step S32, the incidence radiation intensity analyzing method of CPU 14 determines the optimum incidence intensity If of the primary X-ray P minimizing the minimum limit of detection DL in the attention-paid element. Here, as shown by <Equation 6>, the optimum incidence intensity If is set to the initial intensity I0 multiplied by a coefficient α.

$$If = \alpha \cdot I0 \qquad \text{Equation 6}$$

As described above, the net intensity In is proportional to the incidence intensity Ip of the primary X-ray P, further, the sensitivity S is brought into a proportional relationship with the net intensity In as shown by <Equation 3>, and therefore, the sensitivity Sf when the primary X-ray is constituted by the optimum incidence intensity If is shown by <Equation 7> by the coefficient α. Similarly, the first background intensity Ib1*f* when the primary X-ray P is constituted by the optimum incidence intensity If is proportional to the square of the incidence intensity Ip of the primary X-ray P, further, the second background intensity Ib2*f* is proportional to the incidence intensity Ip of the primary X-ray, and therefore, the intensities become respectively as shown by <Equation 8>, <Equation 9>.

$$Sf = \alpha \cdot S \qquad \text{Equation 7}$$

$$Ib1f = \alpha^2 \cdot Ib1 \qquad \text{Equation 8}$$

$$Ib2f = \alpha \cdot Ib2 \qquad \text{Equation 9}$$

Further, the rate τ of dead time is proportional to the incidence intensity Ip of the primary X-ray P by a principle of generating the same, and therefore, the rate τf of dead time when the primary X-ray P is constituted by the optimum incidence intensity If is as shown by <Equation 10> by the coefficient α.

$$\tau f = \alpha \tau \qquad \text{Equation 10}$$

Further, when <Equation 9> through <Equation 11> substitute for <Equation 4>, as shown by <Equation 12>, the minimum limit of detection DL in the optimum incidence intensity If is expressed by the coefficient α, and by determining the coefficient α minimizing the minimum limit of detection DL, the optimum incidence intensity If can be determined from the coefficient a and the initial incidence intensity IpO (S32*a*).

$$DL = \frac{3 \cdot \sqrt{\alpha^2 \cdot Ib1 + \alpha \cdot Ib2 / T \cdot (1 - \alpha \cdot \tau)}}{\alpha \cdot S} \qquad \text{Equation 11}$$

That is, the incidence radiation intensity determining means of CPU 14 substitutes the sensitivity S, the rate τ of dead time, the first background intensity Ib1, and the second background intensity Ib2 calculated at first step of S31 for <Equation 10>. Further, by calculating the coefficient α satisfying a differential equation d (DL)/d α=0 in <Equation 10>, the coefficient α by which the minimum limit of detection DL becomes a minimum value can be calculated, as shown by <Equation 6>, by multiplying the initial intensity I0 by the coefficient α, the optimum incidence intensity If can be determined. In the optimum incidence intensity If determined in this way, when the incidence intensity Ip of the primary X-ray P is reduced thereby, as described above, the sensitivity S is reduced and the minimum limit of detection DL is increased. On the other hand, when the incidence intensity Ip of the primary X-ray P is increased thereby, the influence by the pile up becomes significant, the first background intensity Ib1 caused thereby is rapidly increased and the minimum rate of detection DL is increased. Therefore, by constituting the optimum incidence If by the intensity determined in this way, the influence of the pile up is restrained, and measurement of a plurality of object elements including an attention-paid element can be carried out by minimizing the minimum limit of detection DL.

Specifically, as shown by FIG. 2, CPU 14 multiplies an initial tube current A0 by the coefficient a and supplies the tube current A1 to the filament 5 by the power source 7 such that the primary X-ray P becomes the optimum incidence intensity If as regular detecting step S4. Thereby, the primary X-ray P is irradiated from the X-ray tube 2 to the sample M as an optimum incidence intensity If, and based on the spectrum of the florescent X-ray Q emitted from the sample M and detected by the X-ray detector 3, the content can be specified by calculating the net intensity In of the object element.

As described above, according to the energy dispersion type radiation detection system 1 and the method of specifying the content of the object element using the same of the embodiment, by the control portion 10, based on the spectrum of the initial fluorescent X-ray Q0 detected at initial detecting step, the optimum incidence intensity If of the primary X-ray P can be determined at incidence radiation intensity determining step. Therefore, by irradiating the primary X-ray P to the sample M by the optimum incidence intensity If, the content of the object element can be specified by the optimum minimum limit of detection by restraining the influence of the pile up. Further, even when the contents of a plurality of object elements are specified, by calculating the optimum incidence intensity If minimizing the minimum limit of detection DL with regard to the object element (attention-paid element) minimizing the net intensity In by comparing the net intensities In of the respective object element, the contents can accurately be specified for all of the object elements.

Further, although in first step 31 shown in FIG. 2 as the method of calculating the first background intensity Ib1 and the second background intensity Ib2, the first background intensity Ib1 and the second background intensity Ib2 are calculated by detecting the fluorescent X-ray at initial detecting step and by one more time, the invention is not limited thereto. The first background intensity Ib1 and the second background intensity Ib2 may be calculated from one time detection result by initial detecting step by other operating method. For example, the first background intensity Ib1 may be calculated by predicting the second background intensity Ib2 from an empirical equation in a similar sample and reducing the second background intensity Ib2 from the background intensity Ib read by the spectrum of the fluorescent X-ray. Similarly, although as the method of calculating the sensitivity 5, the fundamental parameter method is used, the invention is not limited thereto but other publicly-known method may be used.

Further, although according to the embodiment, the energy dispersion type radiation detecting system 1 is constituted by the fluorescent X-ray analysis apparatus including the X-ray tube 2 capable of irradiating X-ray at the incidence system and including the X-ray detector 3 capable of detecting the fluorescent X-ray emitted from the sample M at the detecting system, the invention is not limited thereto. For example, the energy dispersion type radiation detecting system 1 may be constituted by a scanning electrode microscope (SEM-EDS) constituting an incidence system by an electron gun and including the X-ray detector 3 capable of detecting the characteristic X-ray emitted from the sample M at a detecting system. Also in this case, CPU 14, of the control portion 10 calculates the coefficient α in correspondence with the optimum incidence intensity If based on the measurement flow. Further, although it is necessary to predict to calculate the sensitivity S similar to the above-described, in this case, the sensitivity S can be calculated by, for example, a publicly-known ZAF method (Atomic number, absorption and fluorescence correction). The ZAF method is a method of predicting the sensitivity in consideration of an influence on an advancing degree of an electron beam by an element or a concentration constituting a sample (atomic number effect), an effect on an easiness in escaping a characteristic X-ray similarly by an element and a concentration (absorption effect), an influence by a specific X-ray and a scattering X-ray by other element (fluorescence exciting effect). Further, by controlling an acceleration voltage and an irradiation current of an electron gun, or a condenser lens thereby, the electron beam can be irradiated to the sample by the optimum incidence intensity If.

Although a detailed description has been given of the embodiment of the invention in reference to the drawings as described above, the specific constitution is not limited to the embodiment but also includes a design change or the like within a range not deviated from the gist of the invention.

What is claimed is:

1. A method of measuring an amount of an element contained in a sample based on a fluorescent x-ray excited out from the sample by an irradiation of a primary x-ray, the method comprising:
   providing a base function defining a lower detection level of measurement in relation to a sensitivity of the measurement and a background intensity of the fluorescent x-ray, wherein the background intensity is a function of a first background intensity effected by a pileup and a second background intensity effected by other causes;
   sequentially irradiating a first and second primary x-rays onto the sample and detecting the respective fluorescent x-rays excited out from the sample by the first and second primary x-rays;
   calculating the first background intensity and the second background intensity based on a difference in intensity between the first and second primary x-rays;
   calculating the sensitivity, based on a spectrum of the fluorescent x-ray excited out by the first primary x-ray;
   calculating an effective sensitivity and an effective background intensity to be exhibited with the primary x-ray irradiated at an optimum intensity, wherein the effective sensitivity is a function of the calculated sensitivity and an intensity ratio between the optimum intensity and the intensity of the first primary x-ray, and the effective background intensity is a function of the calculated first and second background intensities and the intensity ratio;
   using the effective sensitivity and the effective background intensity, solving the base function to derive the intensity ratio which minimizes the lower detection level; and
   irradiating the primary x-ray onto the sample at the optimum intensity determined from the calculated intensity ratio.

2. The method according to claim 1, wherein providing the base function comprises providing the base function so as to define the lower detection level in relation further to an dead time of a detector for detecting the fluorescent x-ray from the sample, and the method further comprises determining the dead time when the detector detects the fluorescent x-ray excited out by the first primary x-ray.

3. The method according to claim 2, wherein providing the base function comprises providing the base function so as to define the lower detection level in relation further to a measurement time spent in measuring the fluorescent x-ray excited out by the first primary x-ray.

4. The method according to claim 3, wherein providing the base function comprises providing the base function represented by the following equation:

$$DL = \frac{3 \cdot \sqrt{\frac{Ib}{T \cdot (1-\tau)}}}{S}$$

where DL represents the lower detection level, Ib represents the background intensity, T represents the time spent in the measurement, $\tau$ represents a ratio between the dead of the detector and the time spent in the measurement, and S is the sensitivity.

5. The method according to claim 1, wherein
calculating the first background intensity and the second background intensity comprises defining the background intensity of the fluorescent x-ray excited out by the first primary x-ray as a sum of the first background intensity and the second background intensity, and defining the background intensity of the fluorescent x-ray excited out by the second primary x-ray as a sum of the first background intensity multiplied by a squire of a ratio of the intensities of the first and second primary x-rays and the second background intensity multiplied by the same ratio, and
calculating the first background intensity and the second background intensity further comprises solving, on the first background intensity and the second background intensity, the definition of the background intensity caused by the first primary x-ray and the definition of the background intensity caused by the second primary x-ray.

6. The method according to claim 5, wherein calculating the sensitivity comprises calculating the sensitivity, using a fundamental parameter method.

7. The method according to claim 1, wherein defining an effective sensitivity comprises defining an effective sensitivity as a multiplicity of the calculated sensitivity and the intensity ratio, and defining the effective background intensity comprises defining the effective background intensity as a sum of the calculated first background intensity multiplied by a square of the intensity ratio and the calculated second background intensity multiplied by the intensity ratio.

8. The method according to claim 1, wherein solving the base function to derive the intensity ratio which minimizes the lower detection level comprises solving the following equation on the intensity ratio:

$$DL = \frac{3 \cdot \sqrt{\frac{\alpha^2 \cdot Ib1 + \alpha \cdot Ib2}{T \cdot (1 - \alpha \cdot \tau)}}}{\alpha \cdot S}$$

where Ib1 represents the first background intensity, Ib2 represents the second background intensity and $\alpha$ represents the intensity ratio.

9. An energy dispersion type radiation detecting system for measuring an amount of an element contained in a sample based on a fluorescent x-ray excited out from the sample by an irradiation of a primary x-ray, the system comprising:
a primary x-ray irradiator configured to irradiate the primary x-ray onto the sample and a detector configured to detect the fluorescent x-ray excited out from the sample by the primary x-ray;
a memory which stores a base function defining a lower detection level of measurement in relation to a sensitivity of the measurement and a background intensity of the fluorescent x-ray, wherein the background intensity is a function of a first background intensity effected by a pileup and a second background intensity effected by other causes;
a primary test operator configured to control the primary x-ray irradiator and the detector in order to sequentially irradiate a first and second primary x-rays onto the sample and detecting the respective fluorescent x-rays excited out from the sample by the first and second primary x-rays;
an intensity calculator configured to calculate the first background intensity and the second background intensity based on a difference in intensity between the first and second primary x-rays;
a sensitivity calculator configured to calculate the sensitivity, based on a spectrum of the fluorescent x-ray excited out by the first primary x-ray;
an effective value determiner configured to determine the calculated sensitivity and calculated background intensity to define an effective sensitivity and an effective background intensity to be exhibited with the primary x-ray irradiated at an optimum intensity, wherein the effective sensitivity is a function of the calculated sensitivity and an intensity ratio between the optimum intensity and the intensity of the first primary x-ray, and the effective background intensity is a function of the calculated first and second background intensities and the intensity ratio;
an optimum intensity calculator configured to solve the base function, using the effective sensitivity and the effective background intensity, to derive the intensity ratio which minimizes the lower detection level; and
a primary test operator configured to irradiate the primary x-ray onto the sample at the optimum intensity determined from the calculated intensity ratio.

10. The system according to claim 9, wherein the base function defines the lower detection level in relation further to an dead time of a detector for detecting the fluorescent x-ray from the sample, and the system further comprises a dead time detector configured to detect the dead time when the detector detects the fluorescent x-ray excited out by the first primary x-ray.

11. The system according to claim 10, wherein providing the base function defines the lower detection level in relation further to a measurement time spent in measuring the fluorescent x-ray excited out by the first primary x-ray.

12. The system according to claim 11, wherein the base function is represented by the following equation:

$$DL = \frac{3 \cdot \sqrt{\dfrac{Ib}{T \cdot (1-\tau)}}}{S}$$

where DL represents the lower detection level, Ib represents the background intensity, T represents the time spent in the measurement, τ represents a ratio between the dead of the detector and the time spent in the measurement, and S is the sensitivity.

13. The system according to claim 9, wherein the intensity calculator defines the background intensity of the fluorescent x-ray excited out by the first primary x-ray as a sum of the first background intensity and the second background intensity, and further defines the background intensity of the fluorescent x-ray excited out by the second primary x-ray as a sum of the first background intensity multiplied by a squire of a ratio of the intensities of the first and second primary x-rays and the second background intensity multiplied by the same ratio, and the intensity calculator solves, on the first background intensity and the second background intensity, the definition of the background intensity caused by the first primary x-ray and definition of the background intensity caused by the second primary x-ray.

14. The system according to claim 13, wherein the sensitivity calculator calculates the sensitivity, using a fundamental parameter method.

15. The system according to claim 9, wherein the effective value determiner determines an effective sensitivity as a multiplicity of the calculated sensitivity and the intensity ratio, and determines the effective background intensity as a sum of the calculated first background intensity multiplied by a square of the intensity ratio and the calculated second background intensity multiplied by the intensity ratio.

16. The system according to claim 9, wherein the optimum intensity calculator solves the following equation on the intensity ratio:

$$DL = \frac{3 \cdot \sqrt{\dfrac{\alpha^2 \cdot Ib1 + \alpha \cdot Ib2}{T \cdot (1 - \alpha \cdot \tau)}}}{\alpha \cdot S}$$

where Ib1 represents the first background intensity, Ib2 represents the second background intensity and α represents the intensity ratio.

* * * * *

UNITED STATES PATENT AND TRADEMARK OFFICE
CERTIFICATE OF CORRECTION

PATENT NO. : 7,529,337 B2
APPLICATION NO. : 11/820893
DATED : May 5, 2009
INVENTOR(S) : Yoshiki Matoba et al.

It is certified that error appears in the above-identified patent and that said Letters Patent is hereby corrected as shown below:

On the Title Page

Item (75), delete "Chiba" and substitute --Chiba-shi-- in its place (all occurrences).

In the Claims

In column 13, claim 2, line 3, after "in relation further to" delete "an" and substitute --a-- in its place.

In column 14, claim 10, around line 59, before "dead time of a detector" delete "an" and substitute --a-- in its place.

Signed and Sealed this

First Day of September, 2009

David J. Kappos
*Director of the United States Patent and Trademark Office*